US00PP36280P2

(12) United States Plant Patent
Head

(10) Patent No.: US PP36,280 P2
(45) Date of Patent: Nov. 26, 2024

(54) ***SALVIA* PLANT NAMED 'Celebration'**

(50) Latin Name: *Salvia officinalis*
Varietal Denomination: Celebration

(71) Applicant: Stephen Head, Chilliwack (CA)

(72) Inventor: Stephen Head, Chilliwack (CA)

( * ) Notice: Subject to any disclaimer, the term of this patent is extended or adjusted under 35 U.S.C. 154(b) by 0 days.

(21) Appl. No.: 18/582,633

(22) Filed: Feb. 20, 2024

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 5/02
See application file for complete search history.

*Primary Examiner* — Kent L Bell
(74) *Attorney, Agent, or Firm* — Weatherly IP Solutions, LLC; James M. Weatherly

(57) ABSTRACT

A new cultivar of *Salvia* plant named 'Celebration' that is distinguishable by its compact well-branched rounded plant habit and bi-colored foliage of 'Celebration' whose leaves are sage-green in color with vibrant golden yellow colored margins. The foliage of 'Celebration' is highly aromatic, especially when crushed, and is characteristic of the scent and flavor of the commonly used culinary herb sage. Plants of 'Celebration' respond to regular pruning and trimming which stimulates rapid and prolific production of desirable juvenile foliage for culinary use, and averts production of undesirable flower stems. A regularly pruned plant of 'Celebration' will fill out and cover the surface of a 1-quart container within 6-8 weeks of transplanting a rooted cutting. A further 4 weeks are required to fill out a 1-gallon container. Plants of 'Celebration' are both heat and drought tolerant when grown in containers or in the landscape.

2 Drawing Sheets

Genus and species: *Salvia officinalis.*
Variety denomination: 'Celebration'.

BACKGROUND

The present disclosure relates to a new and distinct cultivar of *Salvia* plant, also known as a sage, a perennial that is grown for use as an ornamental landscape and container plant. The new variety is known botanically as *Salvia officinalis* and will be referred to hereinafter by the cultivar name 'Celebration'.

'Celebration' originated as a naturally occurring branch sport mutation which was discovered by the inventor in May 2011 as a branch sport on a whole plant of *Salvia officinalis* 'Icterina' (unpatented) which was growing in a container at the inventor's nursery in Chilliwack, British Columbia, Canada. The inventor excised the whole branch and established the branch on its own root system after which the inventor took and rooted internodal softwood cuttings. The newly-established plants exhibited the same foliage coloration as the branch sport and the same plant habit as the sport parent variety.

'Celebration' was first asexually propagated in 2020 in a greenhouse at the inventor's nursery in Chilliwack, British Columbia, Canada using softwood tip cuttings. The inventor has confirmed that 'Celebration' is stable and reproduces true to type in successive generations of asexual reproduction.

SUMMARY

The following traits have been repeatedly observed and represent the distinguishing characteristics of 'Celebration'. 'Celebration' has not been tested under all possible conditions and phenotypic differences may be observed with variations in environmental, climatic, and cultural conditions, without however, any variance in genotype.

1. 'Celebration' exhibits a compact well-branched rounded plant habit.
2. The foliage of 'Celebration' is bi-colored. The leaves of 'Celebration' are sage-green in color with vibrant golden yellow colored margins except that the lower surfaces of the leaves are dull in comparison with the glossy upper surfaces.
3. The foliage of 'Celebration' is highly aromatic, especially when crushed, and is characteristic of the scent and flavor of the commonly used culinary herb sage.
4. Plants of 'Celebration' respond to regular pruning and trimming which stimulates rapid and prolific production of desirable juvenile foliage and averts production of undesirable flower stems.
5. A regularly pruned plant of 'Celebration' will fill out and cover the surface of a 1-quart container within 6-8 weeks of transplanting a rooted cutting. A further 4 weeks are required to fill out a 1-gallon container.
6. Plants of 'Celebration' are both heat and drought tolerant when grown in containers or in the landscape.

DESCRIPTION OF THE PHOTOGRAPHS

The accompanying color photographs illustrate the overall appearance of the new *Salvia* cultivar 'Celebration' showing the colors as true as it is reasonably possible to obtain in colored reproductions of this type. Photographs were taken in September 2023 in Santa Barbara, California from a 12-week-old plant grown outdoors in 1-gallon container, with bi-weekly pruning and without the use of any chemical growth regulators. Colors in the photographs may differ from the color values cited in the detailed botanical description, which accurately describes the actual colors of the new variety 'Celebration'.

DESCRIPTION OF THE NEW VARIETY

Figure 1:
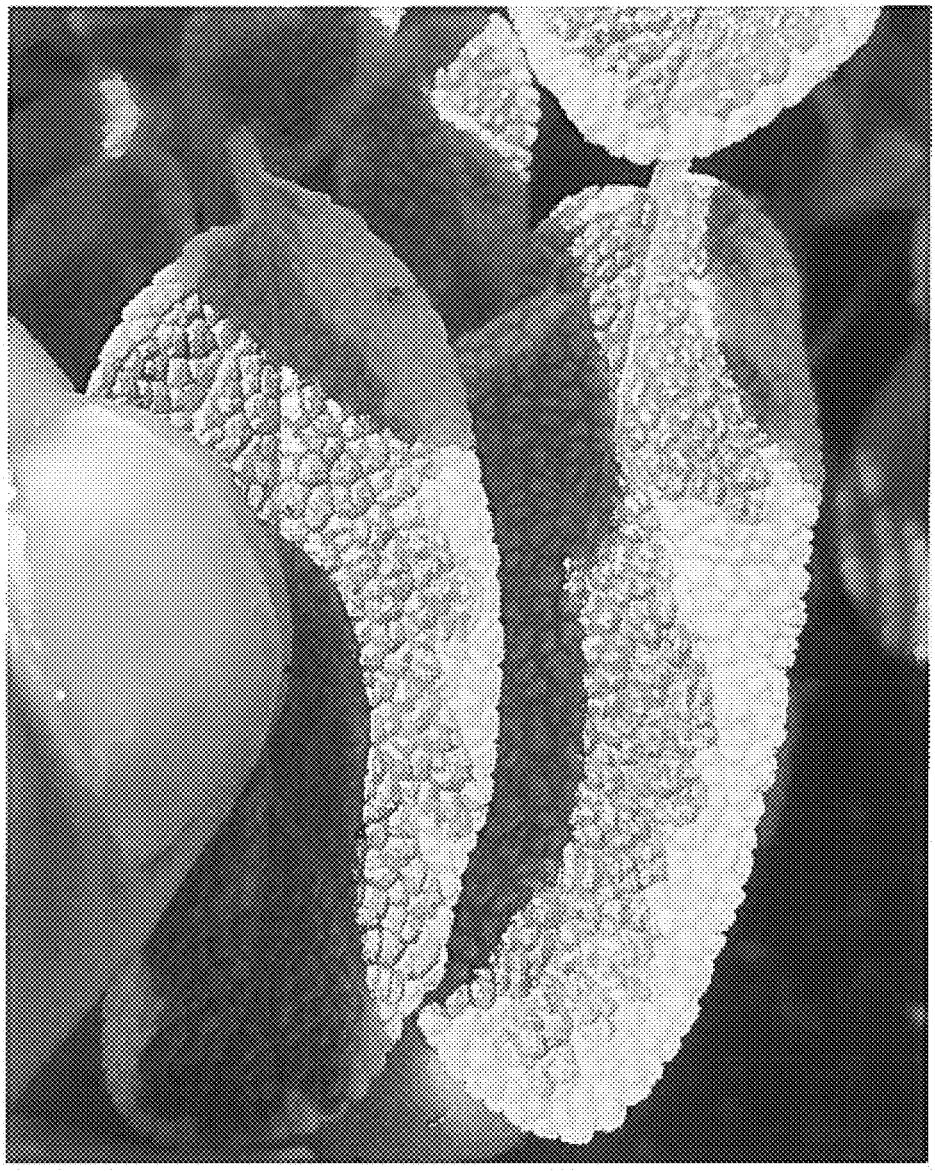
FIG. 1 depicts, on the left, the upper surface of a leaf of 'Celebration' and, on the right, the upper surface of the leaf of the sport parent *Salvia officinalis* 'Icterina' which bear wider golden yellow margins.
Figure 2:
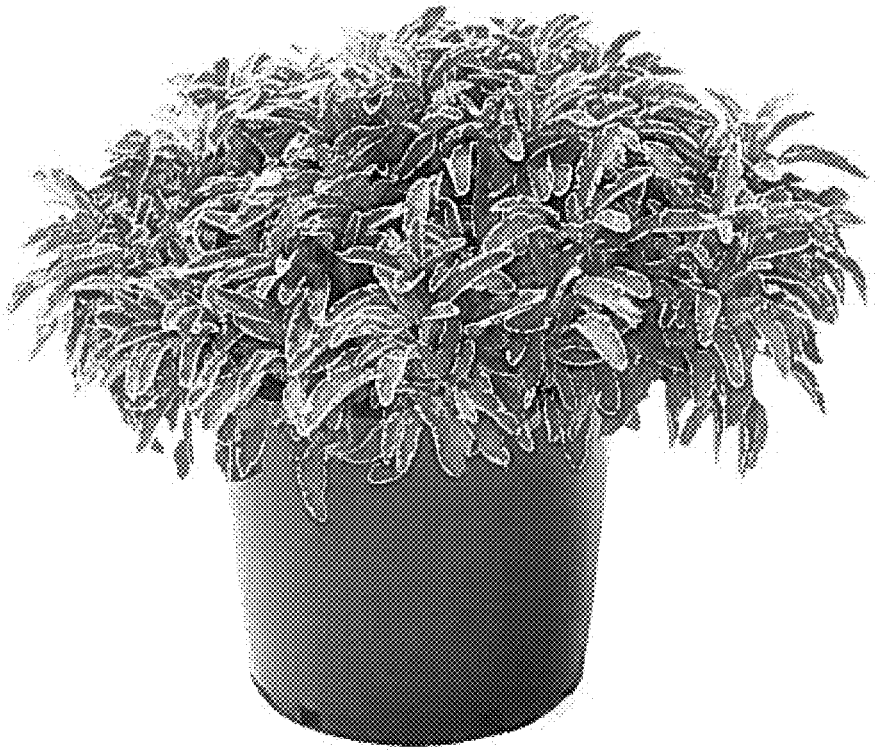
FIG. 2 depicts an entire plant of 'Celebration' which has been regularly pruned from establishment and during growth in a 1-gallon container.

The following detailed descriptions set forth the distinctive characteristics of 'Celebration'. Observations, measurements, values, and comparisons were collected in March 2022 in Santa Barbara, California from a one year old plant which had been growing outdoors in full sun in a 1-gallon container in Santa Barbara, California. Color determinations were made in accordance with The 2007 Royal Horticultural Society Colour Chart from London England, except where general color terms of ordinary dictionary significance are used.

Classification:
- *Family*.—Lamiaceae.
- *Genus*.—*Salvia*.
- *Species*.—*officinalis*.
- *Common name*.—Sage.

Parentage:
- *Sport parent*.—*Salvia officinalis* 'Icterina'.

Plant:
- *Propagation method*.—Softwood internodal cuttings or tip cuttings.
- *Rooting system*.—Fine, branching and fibrous; Color 163D.
- *Vigor*.—Moderate vigor with prolific branching after pruning.
- *Time to develop roots*.—5 days are needed for a cutting to develop roots at recommended rooting temperature of 20° to 22° Centigrade.
- *Crop time*.—Approximately 6 weeks-10 weeks are required to produce a full plant in a one quart container or a one gallon container from planting a rooted cutting.
- *Suggested container sizes*.—1 quart to 1 gallon container.
- *Use*.—Herb for culinary use and as an ornamental container or landscape plant.
- *Type*.—Perennial.
- *Overall dimensions* (*plant canopy*).—After 6-8 week's growth in a 1-gallon container, 12 cm in height and 18 cm in diameter.
- *Cultural requirements*.—Grow in full sun with moderate water and well-draining soil.
- *Hardiness*.—USDA Zone 4.
- *Form*.—Dense rounded and mounded bush.
- *Growth habit*.—Compact.
- *Blooming season*.—An unpruned plant of 'Celebration' will generate flowering stems in late spring and through summer.

Stems (below first pinch):
- *Condition*.—Semi-ripe (stiff, not lignified).
- *Shape*.—Round.
- *Length from base to node of lowest leaf pair*.—1 cm to 2 cm.
- *Diameter*.—3 mm-4 mm.
- *Surface*.—Smooth, pubescent.
- *Color*.—Close to 138C.

Branches:
- *Quantity*.—40-45, of which 6-8 are basal branches. Each basal branch bears 2-4 lateral branches.
- *Basal branch stem shape*.—Square, corners rounded.
- *Basal branch stem length*.—Up to 2 cm. from soil level to first (lowest) leaf pair.
- *Basal branch stem width*.—3 mm-4 mm.
- *Basal branch stem surface*.—Smooth, lightly pubescent.
- *Basal branch stem surface color*.—138C tinged N77D where solar-facing.
- *Lateral branch stem shape*.—Square, corners rounded.
- *Lateral branch stem length*.—Up to 5 cm. from basal node to base of uppermost leaf pair.
- *Lateral branch stem width*.—3 mm-4 mm.
- *Lateral branch stem surface*.—Smooth, lightly pubescent, hairs very fine, less than 1 mm in length, silver in color.
- *Lateral branch stem color*.—138C tinged N77D where solar-facing.
- *Internode length* (*lateral branches*).—Varies between 7 mm and 12 mm.

Leaves:
- *Type, arrangement*.—Simple, opposite.
- *Attachment*.—Petiolate.
- *Quantity per lateral branch*.—5-8 pairs.
- *Shape*.—Elliptic.
- *Length*.—Up to 34 mm.
- *Width*.—Up to 13 mm.
- *Margin*.—Undulating, evenly crenulate, teeth rounded.
- *Thickness*.—Moderate, approximately 0.2 mm.
- *Venation*.—Pinnate, midrib slightly sulcate. Abaxial veins prominently raised.
- *Vein color* (*adaxial surface*).—As adjacent leaf cells 139C and 4C within yellow marginal band.
- *Vein color* (*abaxial surface*).—As adjacent leaf cells 139D and 4D within yellow marginal band.
- *Leaf texture*.—Rugose. Adaxial surface: rugose, smooth, glabrous. Adaxial surface: rugose, smooth, matte.
- *Leaf color* (*adaxial surface*).—139C with yellow marginal band, color 4C.
- *Leaf color* (*abaxial surface*).—139D with yellow marginal band, color 4D.
- *Leaf apex*.—Rounded.
- *Base*.—Obtuse.
- *Fragrance*.—Pleasant sage fragrance when rubbed.
- *Stipules*.—Present at base of lowest leaf attachment, where lateral branch is attached to basal branch). Quantity: 2-3 stipule pairs. Stipule description: Small, petiolate, elliptic, up to 8 mm in length and 3 mm in width. Stipule leaflet color: green 139C to 139D (as leaves) and 4C to 4D as leaf margins. Stipule leaflet surface: Smooth, glabrous. Stipule leaflet margins entire, minutely crenulate.

Leaf petiole:
- *Shape*.—Terete.
- *Length*.—4 cm.
- *Diameter*.—1.5 mm.
- *Texture*.—Puberulent.
- *Color*.—145D.

Inflorescence (peduncle, flowers, reproductive organs, fruit, seed): None produced or observed.

COMPARISON WITH PARENTAL LINE AND KNOWN VARIETY

Both the sport parent 'Icterina' (Also closest known variety) and 'Celebration' exhibit green and yellow variegated foliage which is predominantly sage-green in color surrounded by a golden-yellow margin. The golden-yellow margin of 'Icterina' extends inwards and occupies approximately 20% of the leaf surface area. The golden-yellow margin of 'Celebration' is narrow in comparison and occupies approximately 10% of the leaf surface area. Plants of 'Celebration' are more vigorous and produce more leaves than plants of 'Icterina'.

We claim:

1. A new and distinct variety of *Salvia* plant named 'Celebration' as described and illustrated herein.

* * * * *